(12) United States Patent
Kemp et al.

(10) Patent No.: US 9,155,837 B2
(45) Date of Patent: Oct. 13, 2015

(54) AUTO-INJECTOR

(75) Inventors: Thomas Mark Kemp, Ashwell (GB); Douglas Jennings, Royston (GB); Peter Scudamore, Cambridge (GB); Matthew Ekman, Macclesfield (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 361 days.

(21) Appl. No.: 13/580,216

(22) PCT Filed: Mar. 3, 2011

(86) PCT No.: PCT/EP2011/053159
§ 371 (c)(1),
(2), (4) Date: Feb. 13, 2013

(87) PCT Pub. No.: WO2011/110466
PCT Pub. Date: Sep. 15, 2011

(65) Prior Publication Data
US 2013/0150800 A1    Jun. 13, 2013

(30) Foreign Application Priority Data
Mar. 9, 2010 (EP) .................................... 10155958

(51) Int. Cl.
*A61M 5/20* (2006.01)
*A61M 5/24* (2006.01)
*A61M 5/32* (2006.01)

(52) U.S. Cl.
CPC ............... *A61M 5/2033* (2013.01); *A61M 5/24* (2013.01); *A61M 5/3204* (2013.01);
(Continued)

(58) Field of Classification Search
CPC ... A61M 5/2033; A61M 5/24; A61M 5/3204; A61M 5/3202; A61M 5/3234; A61M 5/326; A61M 2005/202; A61M 2005/206; A61M 2005/208; A61M 2005/2086; A61M 2005/2407; A61M 2005/2496; A61M 2005/3267

USPC .......... 604/131, 134–138, 187, 192, 194–197, 604/207–208, 212, 214, 222, 228, 232
See application file for complete search history.

(56) References Cited

U.S. PATENT DOCUMENTS

| | | | |
|---|---|---|---|
| 6,575,939 B1 * | 6/2003 | Brunel | 604/187 |
| 2001/0005781 A1 * | 6/2001 | Bergens et al. | 604/208 |
| 2002/0095120 A1 | 7/2002 | Larsen et al. | |

FOREIGN PATENT DOCUMENTS

| | | |
|---|---|---|
| GB | 2447339 A | 9/2008 |
| WO | 2004098687 A1 | 11/2004 |

(Continued)

*Primary Examiner* — Theodore Stigell
*Assistant Examiner* — Amber Stiles
(74) *Attorney, Agent, or Firm* — Fish & Richardson P.C.

(57) ABSTRACT

An auto-injector with an interlock mechanism for defining an operation sequence in a manner to allow a lateral trigger button to be operated when a proximal end of the auto-injector is pressed against an injection site. A detector is arranged inside an elongate housing of the auto-injector at the proximal end and slidable in longitudinal direction and biased by a detector spring. A dog is arranged at the trigger button and wherein at least one longitudinal bar is provided, at least one of the bars slidable in longitudinal direction and coupled to the detector for distal movement. A recess for the dog is provided in the bar for allowing the trigger button to be pressed when the detector means is being pushed into the auto-injector and wherein otherwise the dog is engaged with the bar in a manner to prevent the trigger button from being pressed.

12 Claims, 8 Drawing Sheets

(52) U.S. Cl.
CPC ............ *A61M 5/3202* (2013.01); *A61M 5/326* (2013.01); *A61M 5/3234* (2013.01); *A61M 2005/202* (2013.01); *A61M 2005/206* (2013.01); *A61M 2005/208* (2013.01); *A61M 2005/2086* (2013.01); *A61M 2005/2407* (2013.01); *A61M 2005/2496* (2013.01); *A61M 2005/3267* (2013.01)

(56) References Cited

FOREIGN PATENT DOCUMENTS

| WO | 2005021071 A1 | 3/2005 |
| WO | 2008093063 A2 | 8/2008 |
| WO | 2009153542 A1 | 12/2009 |

* cited by examiner

AUTO-INJECTOR

CROSS REFERENCE TO RELATED APPLICATIONS

The present application is a 35 U.S.C. 371 National Application of PCT/EP2011/053159 filed Mar. 3, 2011, which claims priority to European Patent Application No. 10155958.1 filed Mar. 9, 2010, and, the entire contents of which are incorporated entirely herein by reference.

TECHNICAL FIELD

The invention relates to an auto-injector according to the preamble of claim 1.

BACKGROUND OF THE INVENTION

Administering an injection is a process which presents a number of risks and challenges for users and healthcare professionals, both mental and physical.

Injection devices (i.e. devices capable of delivering medicaments from a medication container) typically fall into two categories—manual devices and auto-injectors.

In a manual device—the user must provide the mechanical energy to drive the fluid through the needle. This is typically done by some form of button/plunger that has to be continuously pressed by the user during the injection. There are numerous disadvantages to the user from this approach. If the user stops pressing the button/plunger then the injection will also stop. This means that the user can deliver an underdose if the device is not used properly (i.e. the plunger is not fully pressed to its end position). Injection forces may be too high for the user, in particular if the patient is elderly or has dexterity problems.

The extension of the button/plunger may be too great. Thus it can be inconvenient for the user to reach a fully extended button. The combination of injection force and button extension can cause trembling/shaking of the hand which in turn increases discomfort as the inserted needle moves.

Auto-injector devices aim to make self-administration of injected therapies easier for patients. Current therapies delivered by means of self-administered injections include drugs for diabetes (both insulin and newer GLP-1 class drugs), migraine, hormone therapies, anticoagulants etc.

Auto-injectors are devices which completely or partially replace activities involved in parenteral drug delivery from standard syringes. These activities may include removal of a protective syringe cap, insertion of a needle into a patient's skin, injection of the medicament, removal of the needle, shielding of the needle and preventing reuse of the device. This overcomes many of the disadvantages of manual devices. Forces required of the user/button extension, handshaking and the likelihood of delivering an incomplete dose are reduced. Triggering may be performed by numerous means, for example a trigger button, the action of placing the autoinjector against the skin, or the action of the needle reaching its injection depth. In some devices the energy to deliver the fluid is provided by a spring.

Auto-injectors may be disposable or single use devices which may only be used to deliver one dose of medicament and which have to be disposed of after use. Other types of auto-injectors may be reusable. Usually they are arranged to allow a user to load and unload a standard syringe. The reusable auto-injector may be used to perform multiple parenteral drug deliveries, whereas the syringe is disposed after having been spent and unloaded from the auto-injector. The syringe may be packaged with additional parts to provide additional functionality.

US 2002/0095120 A1 discloses an automatic injection device which automatically injects a pre-measured quantity of fluid medicine when a tension spring is released. The tension spring moves an ampoule and the injection needle from a storage position to a deployed position when it is released. The content of the ampoule is thereafter expelled by the tension spring forcing a piston forward inside the ampoule. After the fluid medicine has been injected, energy stored in the tension spring is released and the injection needle is automatically retracted back to its original storage position.

WO 2009/153542 A1 discloses an injection device comprising a housing adapted to receive a syringe having a discharge nozzle, the syringe being moveable in the housing on actuation of the injection device along a longitudinal axis from a retracted position in which the discharge nozzle is contained within the housing and an extended position in which the discharge nozzle of the syringe extends from the housing through an exit aperture. There is an actuator and a drive adapted to be acted upon by the actuator and in turn act upon the syringe to advance it from its retracted position to its extended position and discharge its contents through the discharge nozzle. A locking mechanism is moveable from an engaged position in a direction into the housing at the exit aperture into a disengaged position. The locking mechanism is adapted to prevent actuation of the device when it is in its engaged position and permit actuation of the device when it is in its disengaged position. The exit aperture is defined by a rim located on an edge of the housing and the locking mechanism comprises a contact surface which is adapted to extend over or around at least a part of the rim.

WO 2008/093063 A2 discloses an auto injector including: a housing; an outlet portion with a needle moveable relative to the housing; a container within the housing for containing medicament; and an actuatable deployment mechanism configured to deploy the outlet portion by moving the outlet portion relative to the housing and to eject medicament contained in the container through the outlet portion. The auto injector is configured to store a volume of fluid and includes a filling mechanism configured to expel the volume of fluid from the outlet portion and subsequently to draw medicament through the outlet portion and into the container. An adaptor fits to the auto injector so as to cover the needle and includes a puncture member configured to puncture a vial, the puncture member providing fluid communication to the needle. The auto injector and adaptor are provided as part of an auto injector pack together with a vial containing a substance which in combination with the liquid forms the medicament and a casing configured to house the vial, the auto injector and the adaptor.

U.S. Pat. No. 6,575,939 discloses a single-use device for injecting a dose of a medicinal product, comprising a syringe and a piston rod provided with a collar housed in a casing formed of two parts, a front part and a rear part, fitted inside each other and capable of sliding in relation to each other over a short traverse between two positions, a retracted position and a forward position. This device additionally includes means for supporting the collar of the piston rod arranged so as to permit, on the one hand, injection under the effect of a propulsion spring in the forward position of the parts of the casing and, on the other hand, backward movement of the syringe inside the casing, after injection, in the retracted position of the said parts of the casing. It also includes means for viewing the supporting means at the end of injection.

In order to prevent needle stick injuries due to inadvertently operated auto-injectors it is desirable to prevent the trigger button from being pressed as long as the auto-injector is not properly positioned against an injection site, i.e. a user's skin.

SUMMARY OF THE INVENTION

It is therefore an object of the present invention to provide an auto-injector with a novel interlock mechanism for defining an operation sequence of the auto-injector.

The object is achieved by an auto-injector according to claim 1.

Preferred embodiments of the invention are given in the dependent claims.

According to the invention an auto-injector for administering a dose of a liquid medicament comprises an elongate housing, a syringe and a trigger button. An interlock mechanism serves for defining an operation sequence of the auto-injector in a manner to allow the trigger button to be operated only when a proximal end of the auto-injector is pressed against an injection site.

A detector means is arranged inside the elongate housing of the auto-injector at the proximal end. The detector means is slidable in longitudinal direction and biased by a detector spring into a position with the detector means protruding beyond the proximal end. A dog is arranged at the trigger button. At least one longitudinal bar is provided in the housing. At least one of the bars is slidable in longitudinal direction and coupled to the detector means for joint movement at least in distal direction. A recess for the dog is provided in the bar for allowing the trigger button to be pressed when the detector means is being pushed into the auto-injector. Otherwise the dog is engaged with the bar in a manner to prevent the trigger button from being pressed.

The interlock mechanism according to the invention is arranged to prevent the trigger button from being pressed as long as the auto-injector is not pressed against the injection site in order to keep the user from activating the auto-injector inadvertently. This increases needle safety and reduces the risk for needle stick injuries and for wasting the medicament without injecting it. The interlock mechanism is arranged to be disengaged by the proximal end of the auto-injector being pressed against the injection site. This skin interlock feature ensures that the device can only be triggered when it is properly positioned for an injection.

The interlock mechanism may be disengaged by pressing the detector means against the injection site. Thus the detector means is translated against the force of the detector spring in distal direction. The interlock mechanism may be arranged to disengage when the detector means is pushed into the auto-injector and essentially on a level with the proximal end of the auto-injector. However, the interlock mechanism may also be arranged to disengage when the detector means is pushed in and still protruding from the proximal end to a lesser extent than without being pushed.

The trigger button is preferably laterally arranged. However, the trigger button may likewise be arranged at a distal end or in another position.

According to the invention at least one of the bars comprises a protruding dog, e.g. protruding inwardly from the bar. A loading bay for a syringe is arranged slidably in longitudinal direction in a manner to advance or retract the syringe. A syringe latch arm having a distal end and a proximal end is pivoted about a latch arm axis transversally arranged to and offset from a longitudinal axis of the auto-injector. The distal end of the latch arm is arranged for engaging behind a shoulder arranged at the loading bay in a manner to prevent the loading bay from being moved in proximal direction. The proximal end of the latch arm is arranged for being engaged by the dog when the detector means is pushed into the auto-injector thus disengaging the distal end of the latch arm from the shoulder.

Once the latch arm is disengaged from the shoulder, the loading bay with the syringe is allowed to be moved in proximal direction. When the detector means is not pushed into the auto-injector, the syringe latch arm prevents the syringe from being advanced.

The detector means may be arranged as an essentially tubular detector sleeve or as a part with at least one tooth protruding beyond the proximal end.

The proximal end of the latch arm and/or the dog for engaging it may comprise a ramp for easing their interaction.

In a preferred embodiment at least one of the bars is arranged as an extension bar attached to the detector means and extending at least almost to a distal end of a proximal portion of the housing when the detector sleeve is pushed into the auto-injector. This extension bar serves for operating the latch arm. Another one of the bars may be arranged in a distal portion of the housing as a transmission bar serving for interacting with the trigger button.

A proximal end of the transmission bar may bear against a distal end of the extension bar when the portions are aligned. Consequently, translation of the detector sleeve is forwarded to the transmission bar when the portions are aligned. This allows for employing the interlock mechanism in reusable auto-injectors comprising housing portions which can be separated for replacing the syringe in the loading bay.

Such a reusable auto-injector for administering a dose of a liquid medicament may comprise:

the elongate housing arranged to contain the syringe with a hollow needle and a stopper for sealing the syringe and displacing the medicament, the housing having a distal end and a proximal end with an orifice intended to be applied against the injection site, wherein the syringe is slidably arranged with respect to the housing, a drive spring capable of, upon activation:
pushing the needle from a covered position inside the housing into an advanced position through the orifice and past the proximal end, and
operating the syringe to supply the dose of medicament, and activating means, i.e. the trigger button arranged to lock the drive spring in a compressed state prior to manual operation and capable of, upon manual operation, releasing the drive spring for injection.

The elongate housing may comprise the distal portion and the proximal portion connected by a hinge, the hinge having a rotational axis offset from a longitudinal axis of the auto-injector and oriented transversally with respect to the longitudinal axis. The portions are rotatable about the hinge relative to each other between an aligned position with their longitudinal axes aligned and a maximum opening angle. The drive spring may be compressed by rotating the portions out of the aligned position towards the maximum opening angle. The activating means are arranged to lock the drive spring in the compressed state when the portions are rotated at least almost by the maximum opening angle. The loading bay for holding the syringe is arranged in the proximal portion, the loading bay accessible from its distal end for loading or unloading the syringe when the portions are rotated out of the aligned position, e.g. when they are rotated by least almost the maximum opening angle.

An alternative embodiment of the auto-injector with the interlock mechanism may have the two portions connectable by other means than the hinge, e.g. a screw connection, bayonet fit, re-priming plunger or lever.

In the context of this specification the term proximal refers to the direction pointing towards the patient during an injection while the term distal refers to the opposite direction pointing away from the patient. When referring to the proximal and distal portion of the auto-injector their respective distal and proximal ends are those that point in the respective direction during an injection, i.e. with the portions aligned. In the terminology of this specification the distal end of the distal portion remains the distal end even if the portions are rotated by the maximum opening angle in such a manner that the distal end of the distal portion essentially points in the same direction as the proximal end of the proximal portion in this situation.

The said auto-injector is a reusable auto-injector, which may be split in two by rotating or 'cocking' the portions about the hinge. On the one hand this rotating action serves for cocking the drive spring, on the other hand it provides access to the loading bay in order to remove a spent syringe and insert a new, unused one. As opposed to conventional reusable auto-injectors, the auto-injector according to the invention involves less user actions to reset it for another drug delivery. Conventional auto-injectors usually require the user to dismantle it after use, load a new syringe, reset the drive spring and reassemble the auto-injector.

Once the activating means has been operated to release the drive spring the auto-injector will advance the syringe and needle thereby inserting the needle into the injection site, e.g. a patient's skin. Furthermore the auto-injector will automatically empty the syringe in order to deliver the medicament.

In a preferred embodiment a lever may be attached with one end to a fixed first pivot in the proximal portion, wherein the other end of the lever may be attached to a second pivot arranged at a sliding shuttle in the distal portion. The sliding shuttle may be translatable in longitudinal direction of the distal portion between a maximum proximal position when the portions are aligned and a maximum distal position when the portions are rotated at least almost by the maximum opening angle, which may be about 180 degrees. A drive collar arranged at a proximal end of the drive spring may be engageable by the sliding shuttle in order to compress the drive spring, i.e. the sliding shuttle pushes the drive collar in a distal direction in the distal portion as the portions are rotated out of alignment thus cocking the drive spring, whose distal end may be grounded inside the distal end of the distal portion. During that cocking process, the mechanical advantage increases as the drive spring is compressed due to the lever action. This is particularly advantageous if the drive spring is a compression spring whose spring force increases with the level of compression. Thus, the user effort required to reset the auto-injector is reduced.

The loading bay is preferably biased in distal direction by a syringe retraction spring. The syringe retraction spring may be a compression spring arranged around the loading bay. It may be arranged to retract the syringe in a manner to hide the needle inside the proximal portion after delivering the dose of medicament by decoupling the plunger from the drive spring. This feature provides post-injection needle safety, i.e. the user is prevented from needle stick injury after removing the auto-injector from the injection site.

In another preferred embodiment a spring and damper unit and a release latch member may be arranged proximally from the drive collar in a manner to allow transmission of the force of the drive spring to the plunger when the portions are aligned. The spring and damper unit may comprise a plunger spring and a viscous damper in parallel. A coefficient of damping of the viscous damper and a spring constant of the plunger spring are specified to allow the plunger spring to be compressed by the force of the drive spring against a counteracting force of the stopper in a time greater than a time required to fully empty the syringe. The counteracting force of the stopper depends on friction between the stopper and the inner wall of the syringe and on the hydrostatic resistance of the liquid medicament being displaced through the hollow needle. The release latch member may be pivoted in the spring and damper unit and arranged to be rotated out of engagement with the plunger by the drive collar when the plunger spring is fully compressed. Force transmission from the drive spring to the plunger is thus interrupted and the syringe retraction spring may retract the syringe and needle. Thus both problems are solved, reliably retracting the hollow needle to a safe position and fully emptying the syringe which is particularly desirable with expensive drugs. Emptying the syringe is also important for dosage accuracy.

Preferably, the viscous damper may comprise a piston fixed to the drive collar by a connecting rod, with the piston having a greater diameter than the connecting rod. A hollow cylinder, with an internal diameter slightly greater than the diameter of the piston, may be arranged around the piston thus allowing the piston and cylinder to reciprocate. A proximal end face of the cylinder may be fully closed and a distal end face of the cylinder may be arranged to seal the cylinder against the connecting rod. Thus, the interior of the cylinder may be divided into two separate cavities by the piston. At least one transfer port may be provided through the piston in a manner to allow a fluid to flow between the distal side of the piston and the proximal side, i.e. from one cavity into the other. The size and number of the transfer ports and the viscosity of the fluid in the cylinder determine the damping characteristics of the viscous damper.

A gasket ring may be arranged to seal the piston against the cylinder in order to avoid uncontrolled leaking of the fluid between the cavities which might lead to less repeatable damping characteristics.

Another gasket ring may be arranged to seal the connecting rod against the distal end face of the cylinder in order to avoid fluid leaking out of the damper which would otherwise in a drift of the damping characteristics due to disappearing liquid and to pollution of the interior of the auto-injector. An air space may be provided in the cylinder, e.g. by only partially filling it with the damping fluid in order to compensate for the volume of the connecting rod as it goes into the cylinder. Otherwise the viscous damper could lock since the volume of fluid displaced by the piston on its proximal side is greater than the volume increase on the distal side due to the volume of the connecting rod. Air or another gas provided in the cylinder in addition to the viscous fluid can be compressed in order to compensate this disparity in volume change. A hydraulic lock situation is thus avoided.

The plunger spring may be arranged in a longitudinal bore in the connecting rod and grounded at its distal end in the drive collar. The proximal end of the plunger spring may bear against the proximal face of the cylinder from inside. Thus, the spring and damper unit is arranged as a compact unit.

The drive collar and the trigger button may be equipped with respective snap arms arranged to snap into each other when the drive spring is sufficiently compressed. The snap arms may be disengaged by pressing the trigger button.

Usually the hollow needle is equipped with a protective needle shield for keeping the needle sterile and preventing it from being mechanically damaged. The protective needle shield is attached to the needle when the syringe is assembled.

In order to prepare the auto-injector for delivering a dose the protective needle shield has to be removed from the needle.

In one embodiment of the invention a cap may be arrangeable at the proximal end of the proximal portion. In the cap barbs may be provided for gripping the protective needle shield. When the cap is removed from the housing in preparation of an injection the protective needle shield is reliably removed without exposing the user to too high a risk to injure themselves.

The barbs may be arranged to snap into a circumferential notch or behind a shoulder of the protective needle shield.

Preferably the barbs are arranged to be constrained by the detector sleeve from moving radially outward and inadvertently disengaging the protective needle cap as long as the cap is arranged at the auto-injector.

The cap may be attachable to the housing by a screw connection. This allows for a low force removal of the protective needle shield.

The housing may have at least one viewing window for inspecting the syringe, or be manufactured from a transparent material.

The auto-injector may preferably be used for subcutaneous or intra-muscular injection, particularly for delivering one of an analgesic, an anticoagulant, insulin, an insulin derivate, heparin, Lovenox, a vaccine, a growth hormone, a peptide hormone, a protein, antibodies and complex carbohydrates.

The term "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, a antibody, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2, H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

Corresponding parts are marked with the same reference symbols in all figures.

DETAILED DESCRIPTION OF PREFERRED EMBODIMENTS

Figure 1:
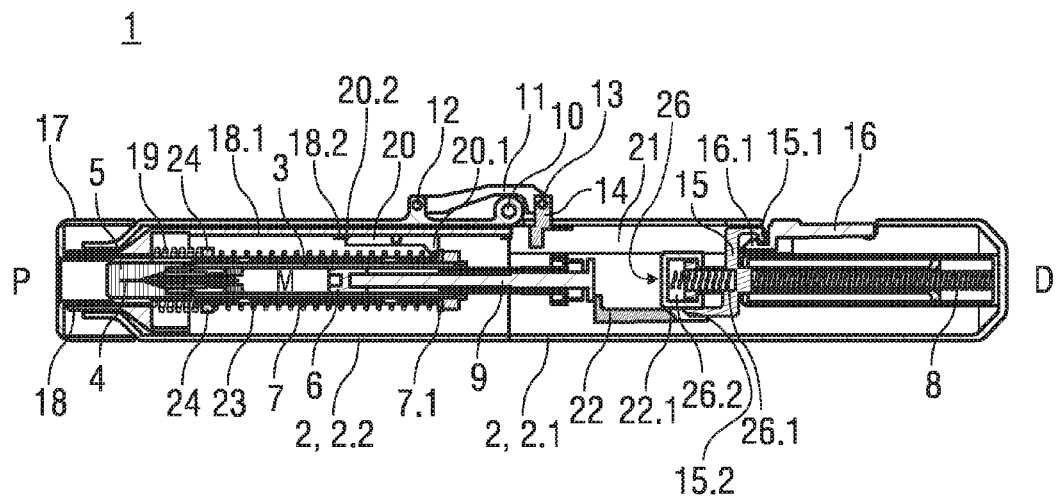
FIG. 1 is a longitudinal section of a reusable auto-injector.

FIG. 1 is a longitudinal section of a reusable auto-injector 1. The auto-injector 1 comprises an elongate housing 2. A disposable syringe 3, e.g. a Unilife® syringe, with a hollow needle 4 is arranged in a proximal portion of the auto-injector 1. When the syringe 3 is assembled a protective needle shield 5 is attached to the needle 4. A stopper 6 is arranged for sealing the syringe 3 distally and for displacing a liquid medicament M through the hollow needle 4. The syringe 3 is held in a tubular loading bay 7. A drive spring 8 in the shape of a compression spring is arranged in a distal portion of the auto-injector 1. A plunger 9 is arranged for transmitting the spring force of the drive spring 8. The drive spring 8 is used for providing axial motion for advancing the syringe 3, inserting the needle 4 into the injection site, i.e. a patient's skin and injecting a dose of medicament M.

In the present embodiment the needle 4 is withdrawn into the syringe 3 once fully emptied. However, a post-injection needle safety function may be alternatively integrated into the auto-injector 1 instead of the syringe 3.

The elongate housing 2 comprises an essentially tubular distal portion 2.1 and an essentially tubular proximal portion 2.2 connected by a hinge 10 so the portions 2.1, 2.2 may be operated similar to a break barrel air rifle.

Figure 2:
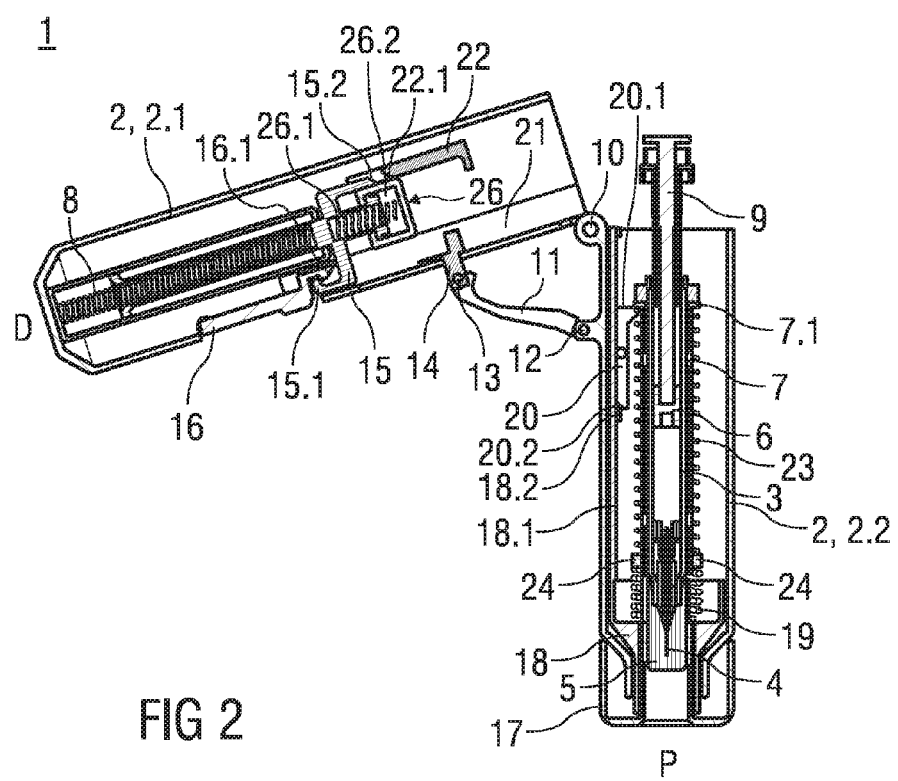
FIG. 2 is a longitudinal section of the auto-injector during loading of a syringe.

FIG. 2 shows how the disposable syringe is loaded into the auto-injector 1. The housing 2 is breached around the hinge 10 so the portions 2.1, 2.2 are not aligned any more. The syringe 3 may now be inserted into the loading bay 7 through the distal opening of the proximal portion 2.2. A lever 11 is attached with one end to a fixed first pivot 12 in the proximal portion 2.2 of the housing 2. The other end of the lever 11 is attached to a second pivot 13 arranged at a sliding shuttle 14 in the distal portion 2.1, the sliding shuttle 14 moveable in longitudinal direction. When the portions 2.1, 2.2 are aligned as in FIG. 1 the sliding shuttle 14 is held in a maximum proximal position by the lever 11. When the housing 2 is breached around the hinge as in FIG. 2 the lever 11 forces the sliding shuttle 14 to move in distal direction D as shown in FIG. 2. In FIG. 2 the drive spring 8 is already in a compressed state. However, if the auto-injector 1 is breached open following an injection the then relaxed drive spring 8 is cocked by the lever 11 since the sliding shuttle 14 bears against a drive collar 15 arranged at a proximal end of the drive spring 8 (cf. FIG. 18). When the sliding shuttle 14 has pushed the drive collar 15 to a maximum distal position a snap arm 15.1 of the drive collar snaps behind a snap arm 16.1. of a trigger button 16. This lever action resets the auto-injector 1 for another injection cycle.

Figure 3:
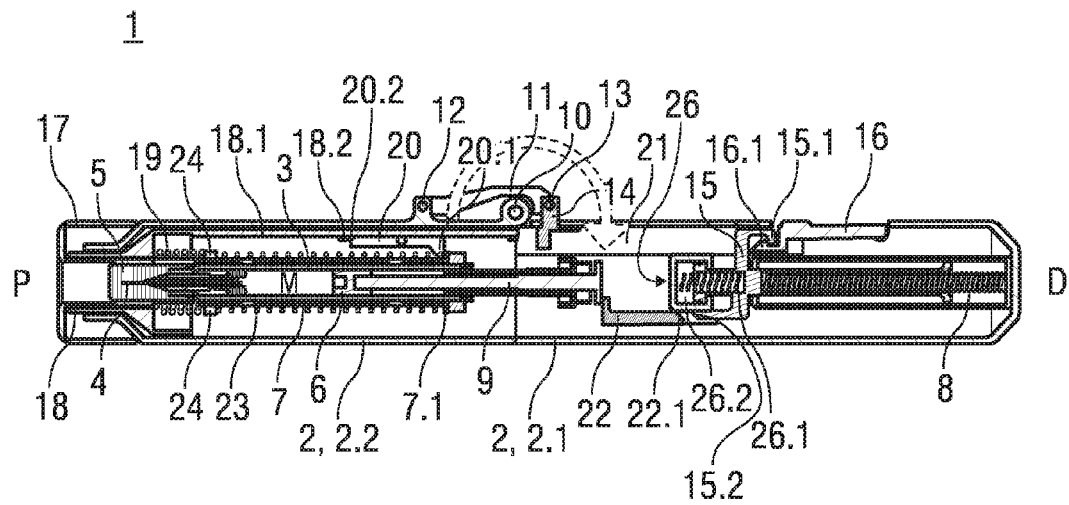
FIG. 3 is the auto-injector in a resetting step after loading.

After cocking the drive spring and inserting the syringe 3 in the manner described the user closes the auto-injector 1 by rotating the distal portion 2.1 about the hinge 10 until its longitudinal axis is aligned to the longitudinal axis of the proximal portion 2.2 as shown in FIG. 3. As the auto-injector 1 is closed, the sliding shuttle 14 translates in proximal direction P within the distal portion 2.1. A locking mechanism (not illustrated) may be provided for locking the two portions 2.1, 2.2 in a coaxial position. An example mechanism may comprise a cylindrical sleeve mounted around the external surface of the housing 2 constrained to translate along the longitudinal axis. To lock the auto-injector 1, once the syringe 3 had been loaded, the sleeve may be positioned across the joint between the distal portion 2.1 and the proximal portion 2.2 thereby preventing rotation about the hinge 10. The sleeve may be sprung loaded such that it automatically locks the portions 2.1, 2.2 coaxially upon aligning them.

Figure 4:
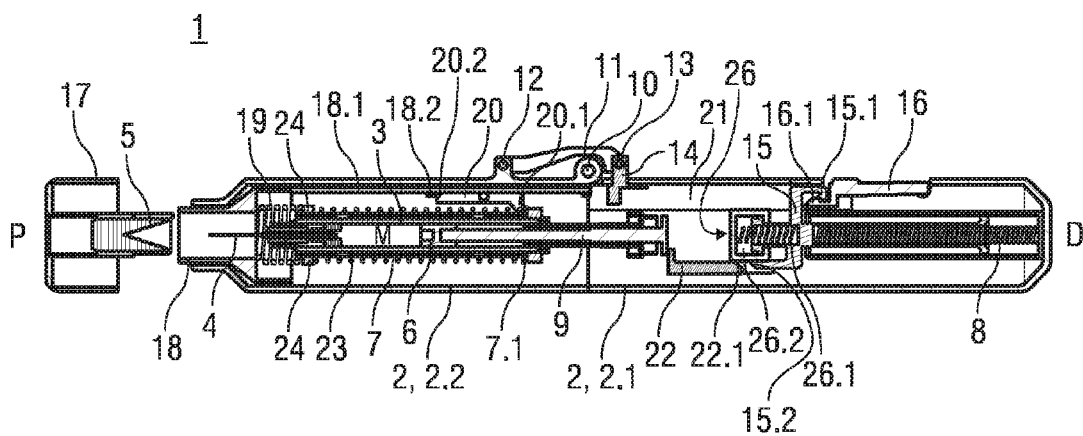
FIG. 4 is the auto-injector during removal of a cap and a rigid needle shield.
Figure 5A:
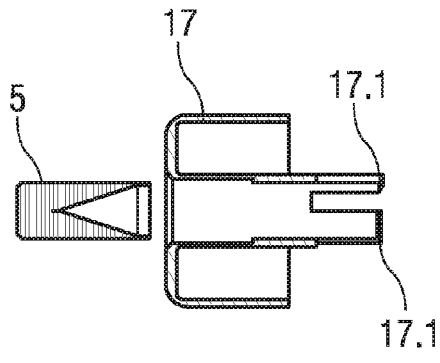
FIG. 5 shows the cap and rigid needle shield in different stages of operation.
Figure 5B:
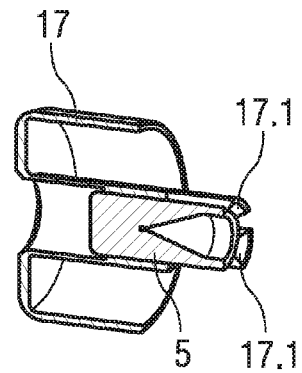
Figure 5C:
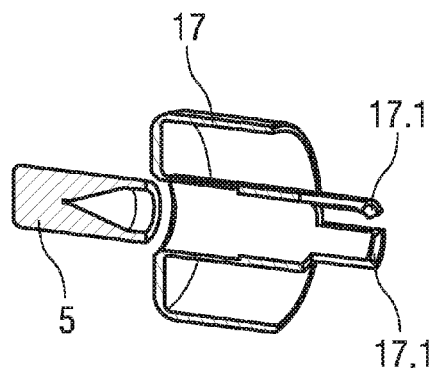

In FIG. 4 the auto-injector 1 is shown during removal of a cap 17 which had been attached to a proximal end P of the proximal portion 2.2. Barbs 17.1 on the cap (see FIGS. 5a, b) constrained from moving outward by a detector sleeve 18 slidably arranged at the proximal end P inside the proximal portion 2.2 grip the protective needle shield 5 thus removing the protective needle shield 5 with the cap 17. Once the cap 17 is removed, the barbs 17.1 are no longer constrained so the protective needle shield 5 is released and may be easily removed from the cap 5 (see FIG. 5c).

Figure 6:
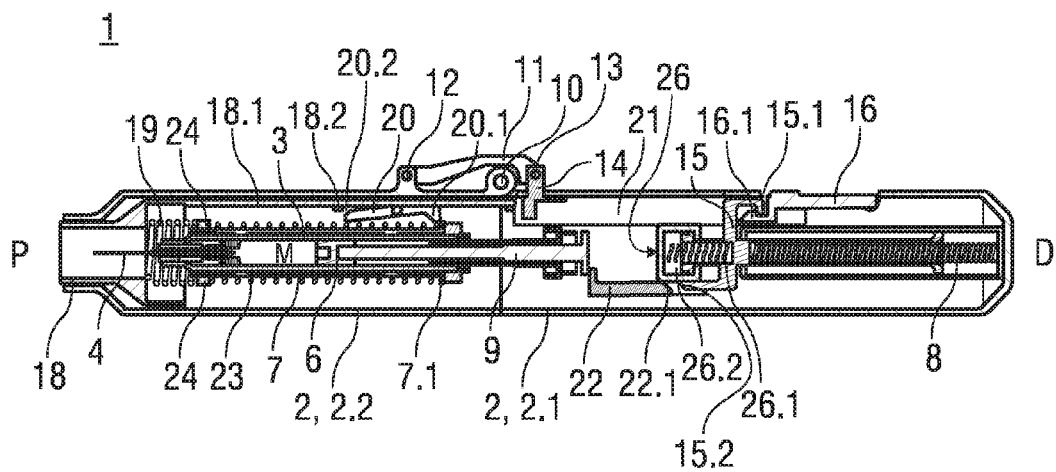
FIG. 6 is the auto-injector pressed against an injection site after the cap and rigid needle shields have been removed.
Figure 7:
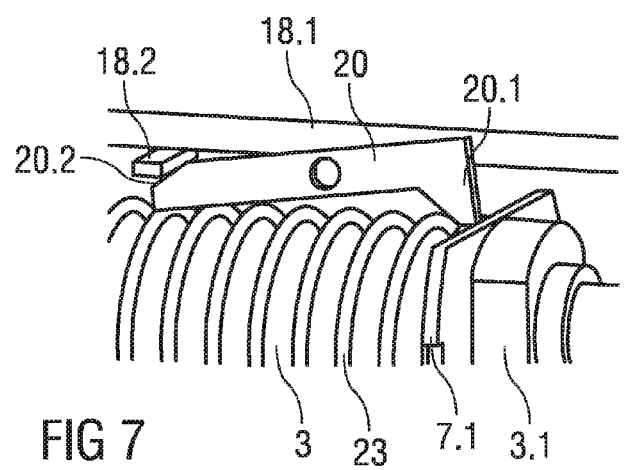
FIG. 7 is a perspective detail view of a syringe interlock with a protective sleeve.
Figure 8:
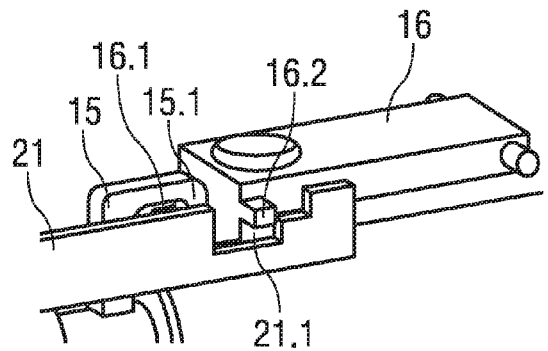
FIG. 8 is a perspective detail view of a trigger button interlock with the protective sleeve.
Figure 9:
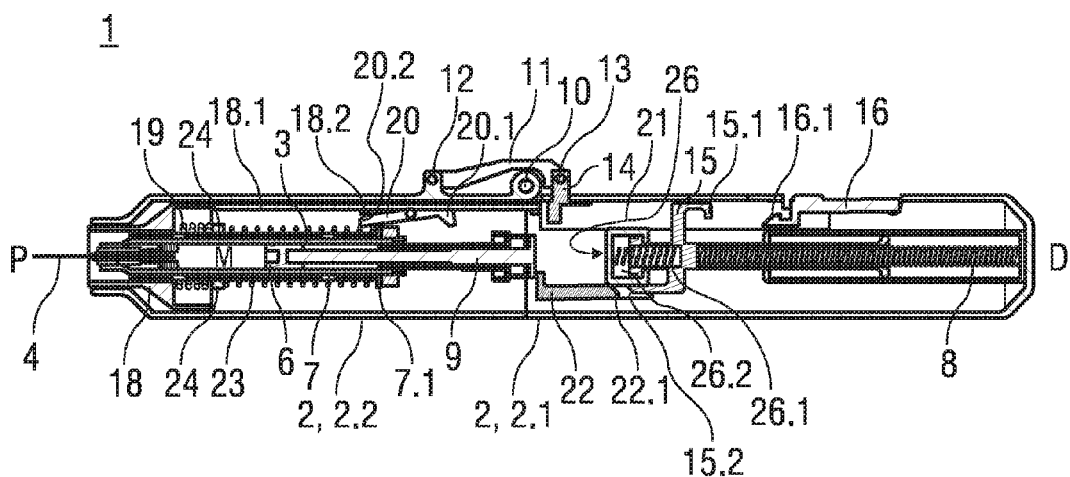
FIG. 9 is the auto-injector during actuation by means of the trigger button.

FIGS. 6, 7 and 8 show details of an interlock mechanism for defining a sequence of operation of the auto-injector 1.

Following the removal of the cap 17 the user places the proximal end of the auto-injector 1 against an injection site, i.e. the user's skin. This causes the detector sleeve 18 to translate in distal direction against the bias of a detector spring 19 (see FIG. 6). As the detector sleeve 17 translates, first latch features and second latch features are released. The first and second latch features prevent the user from accidentally actuating the auto-injector 1 when it is not in contact with the injection site and during a loading and cocking step.

The first latch features comprise a syringe latch arm 20 transversally pivoted about halfway between its ends, the distal end having a nose 20.1 for engaging behind a shoulder 7.1 arranged at the loading bay 7 in a manner to prevent the loading bay 7 from being moved in proximal direction P (see FIG. 7 for details). The proximal end of the syringe latch arm 20 comprises a ramp 20.2. The detector sleeve 18 comprises a longitudinal extension bar 18.1 extending at least almost to the distal end of the proximal portion 2.2 when the detector sleeve 18 is pushed into the auto-injector 1 and essentially on a level with the proximal end P. A dog 18.2 protrudes inwardly from the extension bar 18.1 in a manner to engage the ramp 20.2 when the detector sleeve 18 is pushed into the auto-injector 1, thereby pushing the proximal end of the syringe latch arm 20 inwardly and the distal end of the syringe latch arm 20 outwardly so the nose 20.1 is disengaged from the shoulder 7.1. Thus the loading bay 7 is no longer constrained from being moved in proximal direction P. As long as the detector sleeve 18 is not pushed back the dog 18.2 does not interact with the ramp 20.2. A spring may be arranged for keeping the nose 20.1 engaged with the shoulder 7.1 in this situation (not illustrated).

In another embodiment the latch arm 20 may have a straight end instead of the ramp in which case a ramp may be provided at the dog 18.2. In yet another embodiment both the latch arm 20 and the dog 18.2 may have ramps.

The second latch features are part of a transmission bar 21 arranged in the distal portion 2.1 and slidable in longitudinal direction. When the portions 2.1, 2.2 are coaxially aligned a proximal end of the transmission bar 21 bears against a distal end of the extension bar 18.1. For this purpose the transmission bar 21 may be biased by a spring in proximal direction (not illustrated). Near a distal end of the transmission bar 21 a recess 21.1 is provided for engaging a dog 16.2 arranged at the trigger button 16 (see FIG. 8 for details). Before the detector sleeve 18 is pushed into the auto-injector 1 (cf. FIG. 1) the transmission bar 21 is in a proximal position thus engaging the dog 16.2 in a manner to prevent the trigger button 16 from being pushed inwardly at its proximal end. The distal end of the trigger button 16 is pivoted in the distal portion 2.1. When the detector sleeve 18 is pushed into the auto-injector 1 the translation is forwarded by the extension bar 18.1 to the transmission bar 21 so the dog 16.2 of the trigger button 16 finds some clearance in the recess 21.1 thus allowing the proximal end of the trigger button 16 to be pushed inward.

Figure 10:
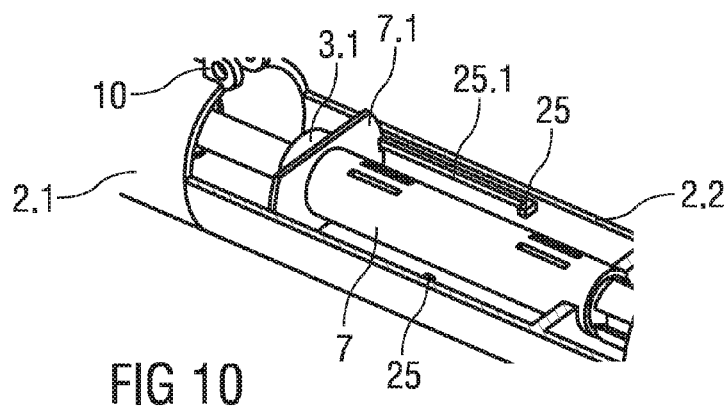
FIG. 10 is a perspective detail view of a loading bay.
Figure 11:
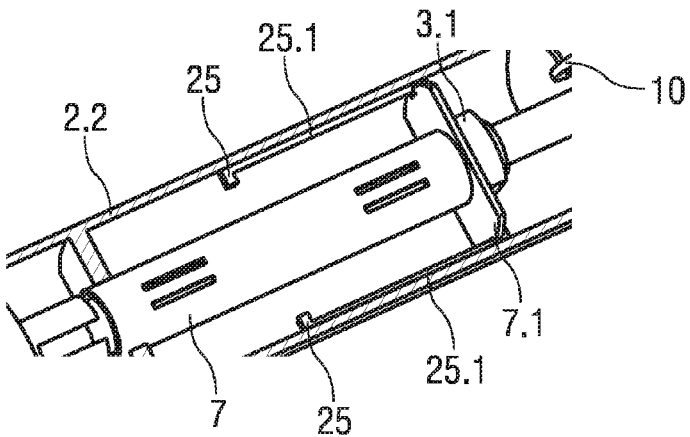
FIG. 11 is another perspective detail view of the loading bay.

In order to deliver an injection the user depresses the trigger button 16. As the proximal end of the trigger button 16 moves inward the snap arms 15.1, 16.1 disengage thus releasing the drive collar 15 and allowing the drive spring 8 to extend. The force from the drive spring 8 is transferred through the drive collar 15 and a release latch member 22 to the plunger 9. The friction between the stopper 6 and the inner wall of the syringe 3 opposes relative motion between them. This friction is greater than a sum of the force of a syringe retraction spring 23 arranged between the shoulder 7.1 of the loading bay 7 and a protrusion 24 in the proximal portion 2.2 and a needle insertion force between the needle 4 and the patient's skin. Hence the needle 4 is inserted into the user's skin without medicament leaking out of the needle's tip (wet injection). An insertion depth is controlled by a flange or shoulder 7.1 of loading bay 7 contacting a stop 25 arranged in the proximal portion 2.2 (see FIGS. 10 and 11). The stop 25 or the two stops 25 may be arranged at a proximal end of a respective longitudinal rib 25.1 arranged in the proximal portion 2.2. The loading bay flange 7.1 may have recesses for rotationally fixing the loading bay flange 7.1 by the longitudinal ribs 25.1.

Once the finger flange 3.1 contacts the stops 25, the force of the drive spring 8 acting on the stopper 6 is sufficient to overcome friction so the emptying of the syringe contents commences.

The drive collar 15 is coupled to the release latch member 22 through a spring and damper unit 26 comprising a plunger spring 26.1 in parallel with a viscous damper 26.2. A coefficient of damping of the viscous damper 26.2 is specified such that a time taken to fully compress the plunger spring 26.1 is greater than a time required to fully empty the syringe 3. This means the stopper 6 will always fully empty the syringe 3.

Figure 15:
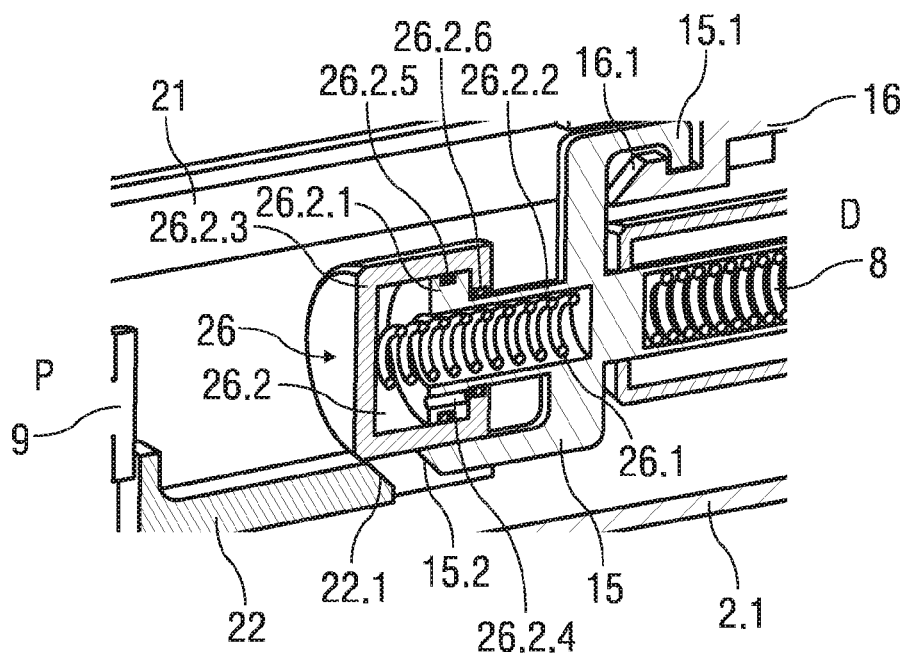
FIG. 15 is a perspective view of the damped delay member of FIG. 13.
Figure 16:
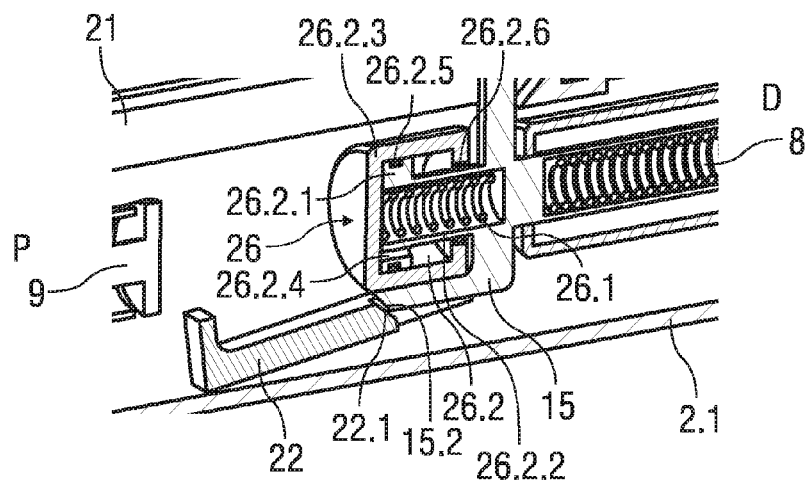
FIG. 16 is a perspective view of the damped delay member of FIG. 14.
Figure 17:
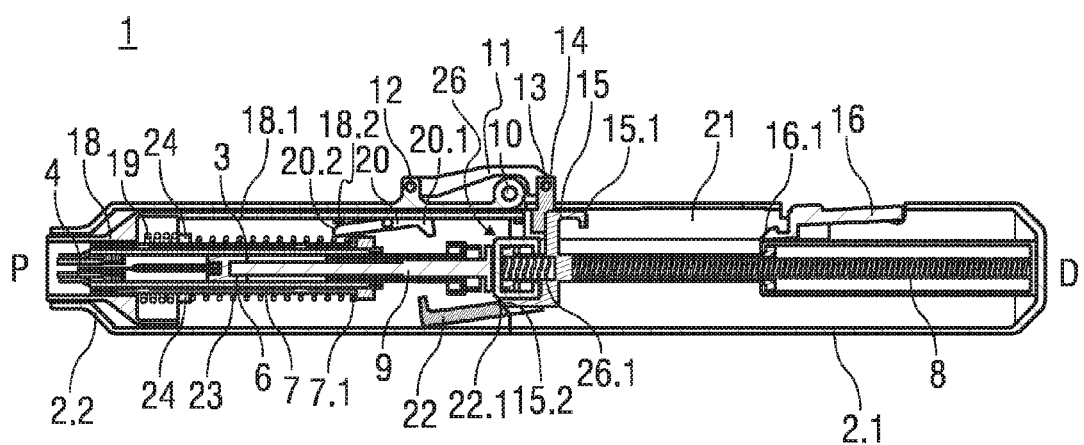
FIG. 17 is the auto-injector when being removed from the injection site.

In the FIGS. 15 and 16 the spring and damper unit 26 is shown in detail. The viscous damper 26.2 comprises a piston 26.2.1 fixed to the drive collar 15 by a connecting rod 26.2.2, the piston 26.2.1 having a greater diameter than the connecting rod 26.2.2. A hollow cylinder 26.2.3 with an internal diameter slightly greater than the diameter of the piston 26.2.1 is arranged around the piston 26.2.1 so the piston 26.1.1 and cylinder 26.2.3 may reciprocate. A proximal end face of the cylinder 26.2.3 is fully closed. A distal end face is arranged to seal the cylinder 26.2.3 against the connecting rod 26.2.2. A small transfer port 26.2.4 is provided through the piston 26.2.1 in longitudinal direction allowing a fluid to flow from the distal side of the piston 26.2.1 to the proximal side and vice versa. Respective gasket rings 26.2.5 and 26.2.6 are arranged to seal the piston 26.2.1 against the cylinder 26.2.3 and the connecting rod 26.2.2 against the hole in the distal end face of the cylinder 26.2.3. The piston 26.2.1 and the distal face wall are provided with respective circumferential notches in order to hold the gasket rings 26.2.5, 26.2.6 in place. There may be more than one transfer port 26.2.4 through the piston 26.2.1. The size of the transfer port 26.2.4 controls the damper characteristics. The fluid may be one of air, another gas, a liquid, grease, e.g. silicone grease. If an incompressible fluid, such as a liquid is used, an air pocket may be provided in the cylinder 26.2.3 in order to compensate for the disparity in volume change at the proximal and the distal side of the piston 26.2.1 during translation.

The plunger spring 26.1 is arranged in a longitudinal bore in the connecting rod 26.2.2 and grounded at its distal end in the drive collar 15. The proximal end of the plunger spring 26.1 bears against the proximal face of the cylinder 26.2.3 from inside. Hence the cylinder 26.2.3 may be translated towards the drive collar 15 against the force of the plunger spring 26.1 and the plunger spring 26.1 may push the cylinder 26.2.3. away from the drive collar 15.

The release latch member 22 is distally pivoted in the spring and damper unit 26, particularly in the cylinder 26.2.3.

Figure 12:
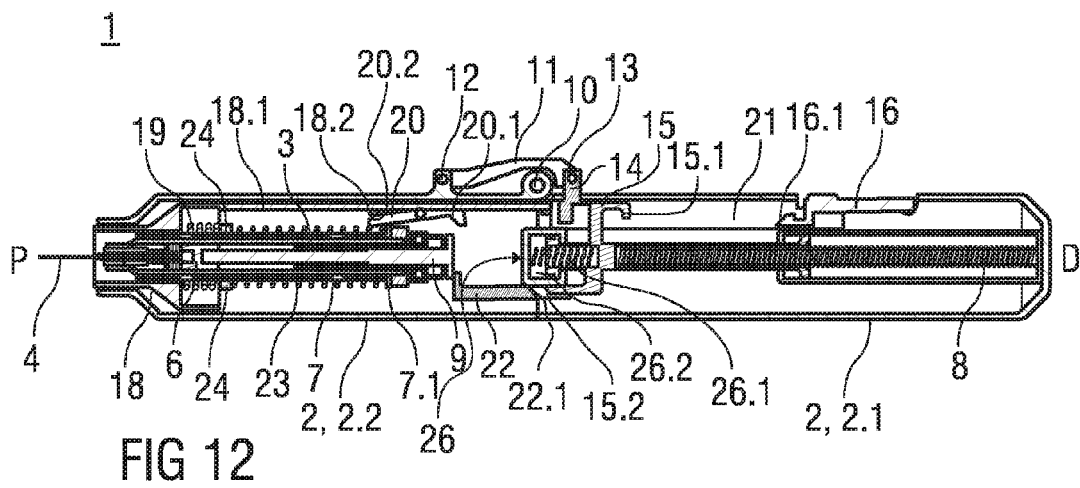
FIG. 12 is the auto-injector near the end of an injection stroke.
Figure 13:
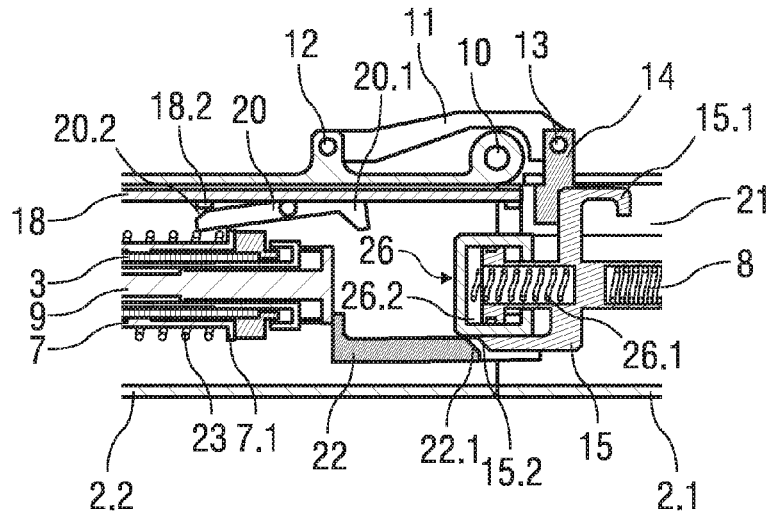
FIG. 13 is a detail view of a damped delay member near the end of the injection stroke.
Figure 14:
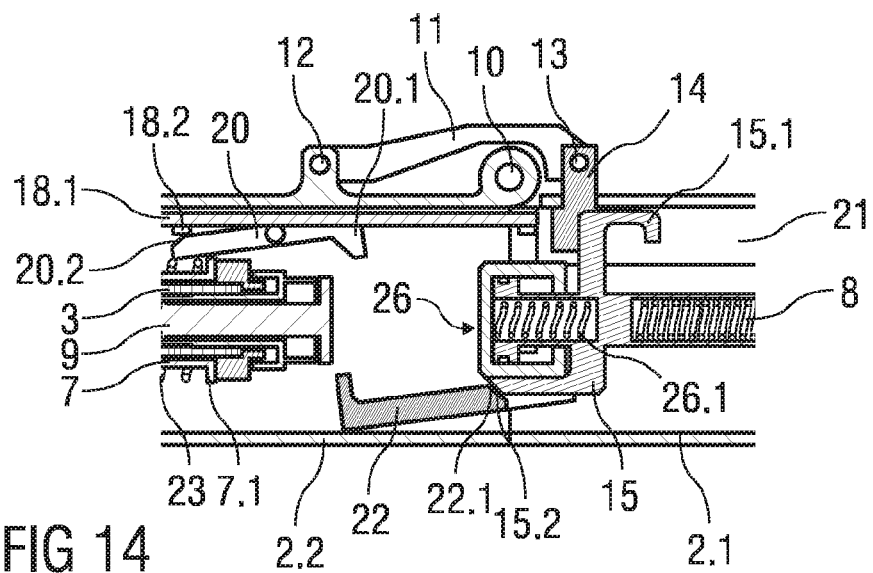
FIG. 14 is a detail view of the damped delay member decoupled from the syringe after the end of the injection.

Once the syringe 3 is fully emptied and the plunger spring 26.1 is fully compressed, a ramp 15.2 on the drive collar 15 contacts a ramp 22.1 on the release latch member 22 thus rotating the release latch member 22 outward and consequently decoupling the drive spring 8 from the plunger 9 (see FIGS. 14 and 16).The needle 4 is withdrawn inside the syringe 3. This may be achieved by the stopper 6 gripping the distal end of the needle 4. The stopper 6 may be pulled in distal direction by means of a spring arranged inside the syringe 3 (not illustrated in the figures). The needle 4 is thus pulled into the syringe 3 and the plunger 9 pushed out in distal direction D into the gap vacated by the latch member. In order to enable both the withdrawal of the needle 4 and the syringe 3 sufficient space has to be provided for the distal end of the plunger 9 towards the spring and damper unit 26. This is achieved by appropriately selecting the length of the release latch member 22. Due to the interrupted force propagation the plunger spring 26.1 will now return the cylinder 26.2.3 to its initial position for further injections as shown in FIGS. 12 and 15.

Figure 18:
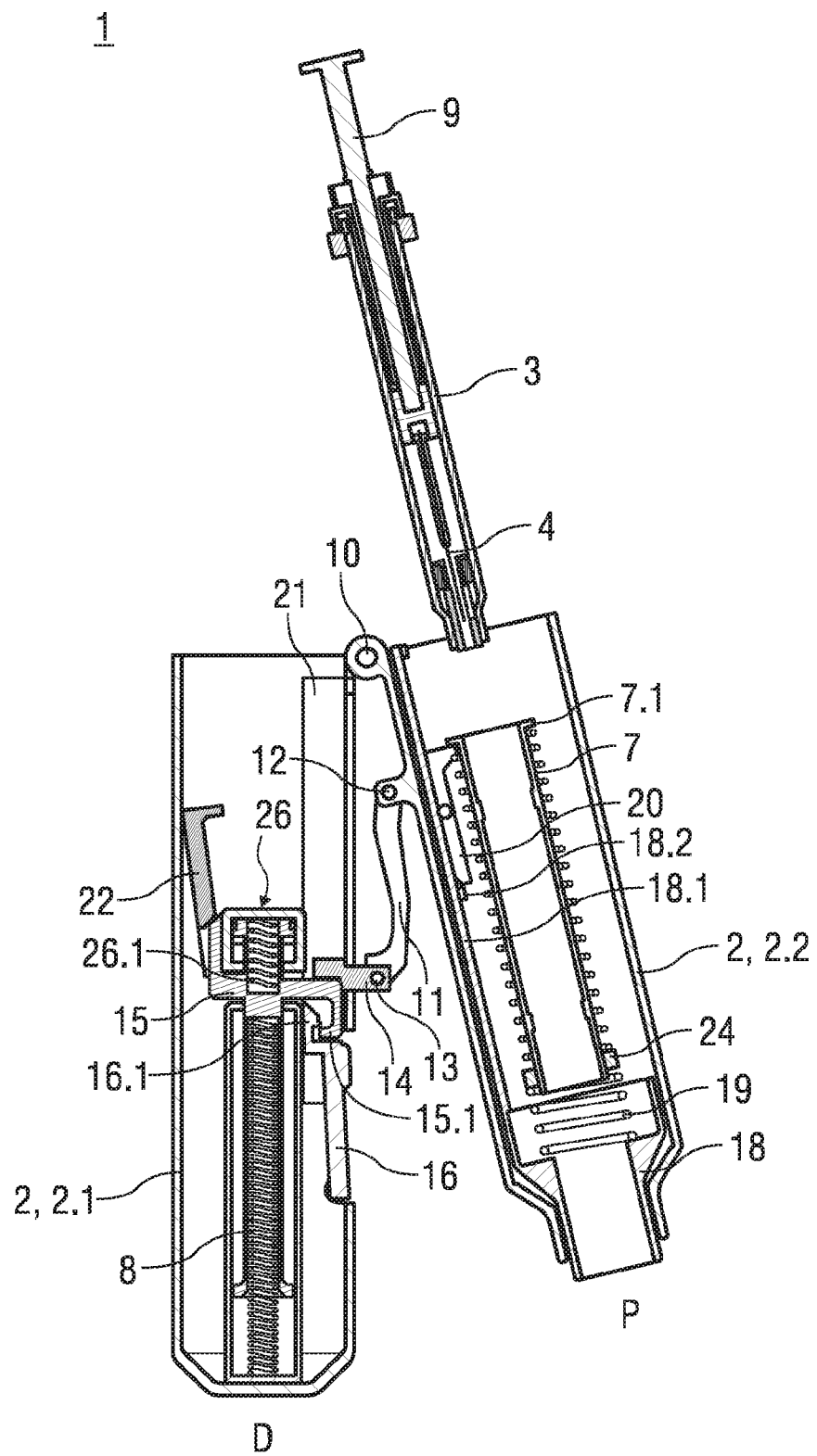
FIG. 18 is the auto-injector during removal of the spent syringe.

The lever action described above is reversed, i.e. the distal portion 2.1 is rotated about the hinge 10 with respect to the proximal portion 2.2 thus allowing access to the loading bay 7 (see FIG. 18). As the auto-injector 1 is hinged in two, the lever 11 translates the sliding shuttle 14 in distal direction of the distal portion 2.1. The sliding shuttle 14 contacts the drive collar 15 and compresses the drive spring 8 in preparation for further injections.

Upon full opening, the snap arms 15.1 and 16.1 of the drive collar 15 and the trigger button 16 snap into each other thus preventing the drive spring 8 from expanding. The emptied syringe 3 may now be safely removed from the loading bay 7.

The spring and damper unit 26 may now return to its initial state under the force of the plunger spring 26.1.

The detector sleeve 18 is pushed in proximal direction P of the proximal portion 2.2 under load of the compressed detector spring 19. The detector spring 19 may be grounded in the protrusion 24.

Although the figures illustrate a syringe 3 with a retracting needle, which ensures needle safety at all times even when changing the disposable syringe, the auto-injector 1 would also work with a fixed needle syringe, such as a Hypak syringe as well.

LIST OF REFERENCES 1 auto-injector
2 elongate housing
2.1 distal portion
2.2 proximal portion
3 syringe
3.1 finger flange
4 hollow needle
5 protective needle shield
6 stopper
7 loading bay
7.1 shoulder, flange
8 drive spring
9 plunger
10 hinge
11 lever
12 first pivot
13 second pivot
14 sliding shuttle
15 drive collar
15.1 snap arm
15.2 ramp
16 trigger button
16.1 snap arm
16.2 dog
17 cap
17.1 barbs
18 detector sleeve
18.1 extension bar
18.2 dog
19 detector spring
20 syringe latch arm
20.1 nose
20.2 ramp
21 transmission bar
21.1 recess
22 release latch member
22.1 ramp
23 syringe retraction spring
24 protrusion
25 stop
25.1 longitudinal rib
26 spring and damper unit
26.1 plunger spring
26.2 viscous damper
26.2.1 piston
26.2.2 connecting rod 26.2.3 hollow cylinder
26.2.4 transfer port
26.2.5 gasket ring
26.2.6 gasket ring
D distal end, distal direction
M medicament
P proximal end, proximal direction

The invention claimed is:

1. An auto-injector for administering a dose of a liquid medicament (M), comprising an elongate housing, a syringe and a trigger button, wherein an interlock mechanism is provided for defining an operation sequence of the auto-injector in a manner to allow the trigger button to be operated only when a proximal end (P) of the auto-injector is pressed against an injection site, wherein a detector means is arranged inside the elongate housing at the proximal end (P), the detector means slidable in longitudinal direction and biased by a detector spring into a position with the detector means protruding beyond the proximal end (P), wherein a dog is arranged at the trigger button and wherein at least one longitudinal bar is provided, at least one of the bars slidable in longitudinal direction and coupled to the detector means for joint movement at least in distal direction (D), wherein a recess for the dog is provided in the bar for allowing the trigger button to be pressed when the detector means is being pushed into the auto-injector and wherein otherwise the dog is engaged with the bar in a manner to prevent the trigger button from being pressed, wherein a loading bay is arranged slidable in longitudinal direction in the auto-injector in a manner to advance or retract the syringe, characterized in that at least one of the bars comprises a dog protruding from the bar wherein a syringe latch arm having a distal end and a proximal end is pivoted about a latch arm axis transversally arranged to and offset from a longitudinal axis of the auto-injector, wherein the distal end of the latch arm is arranged for engaging behind a shoulder arranged at the loading bay in a manner to prevent the loading bay from being moved in proximal direction (P) and wherein the proximal end of the latch arm is arranged for being engaged by the dog when the detector means is pushed into the auto-injector thus disengaging the distal end of the latch arm from the shoulder, the auto-injector further comprising:

the elongate housing arranged to contain the syringe with a hollow needle and a stopper for sealing the syringe and displacing the medicament (M), the housing having a distal end (D) and a proximal end (P) with an orifice intended to be applied against an injection site, wherein the syringe is slidably arranged with respect to the housing, a drive spring capable of, upon activation:
pushing the needle from a covered position inside the housing into an advanced position through the orifice and past the proximal end (P), and
operating the syringe to supply the dose of medicament (M), and an activating means arranged to lock the drive spring in a compressed state prior to manual operation and capable of, upon manual operation, releasing the drive spring for injection, the elongate housing comprising a distal portion and a proximal portion connected by a hinge, the portions rotatable about the hinge relative to each other between an aligned position and a maximum opening angle, wherein the drive spring is compressed by rotating the portions out of the aligned position towards the maximum opening angle, wherein the activating means are arranged to lock the drive spring in the compressed state when the portions are rotated at least almost to the maximum opening angle and wherein the loading bay for holding the syringe is arranged in the proximal portion, the loading bay being accessible from its distal end for loading or unloading the syringe when the portions are rotated out of the aligned position, characterized in that a lever is attached with one end to a fixed first pivot in the proximal portion, wherein the other end of the lever is attached to a second pivot arranged at a sliding shuttle in the distal portion, the sliding shuttle translatable in longitudinal direction of the distal portion between a maximum proximal position when the portions are aligned and a maximum distal position when the portions are rotated at least almost by the maximum opening angle, wherein a drive collar arranged at a proximal end of the drive spring is engageable by the sliding shuttle in order to compress the drive spring.

2. The auto-injector according to claim 1, characterized in that the detector means is arranged as a detector sleeve.

3. The auto-injector according to claim 1, characterized in that the dog and/or the proximal end of the latch arm comprise a ramp.

4. The auto-injector according to claim 1, characterized in that one of the bars is arranged as an extension bar attached to the detector means and extending at least almost to a distal end of a proximal portion of the housing when the detector sleeve is pushed into the auto-injector and wherein another one of the bars is arranged in a distal portion of the housing as a transmission bar.

5. The auto-injector according to claim 1, characterized in that the drive spring is arranged as a compression spring.

6. The auto-injector according to claim 1, characterized in that a spring and damper unit and a release latch member are arranged proximally from the drive collar in a manner to allow transmission of the force of the drive spring via a plunger to the stopper, wherein the spring and damper unit comprises a plunger spring and a viscous damper in parallel, wherein a coefficient of damping of the viscous damper is specified to allow the plunger spring to be compressed by the force of the drive spring against a counteracting force of the stopper in a time greater than a time required to fully empty the syringe, wherein the release latch member is pivoted in the spring and damper unit and arranged to be rotated out of engagement with the plunger by the drive collar when the plunger spring is fully compressed.

7. The auto-injector according to claim 6, characterized in that the viscous damper comprises a piston fixed to the drive collar by a connecting rod, the piston having a greater diameter than the connecting rod, wherein a hollow cylinder with an internal diameter slightly greater than the diameter of the piston is arranged around the piston thus allowing the piston and cylinder to reciprocate, wherein a proximal end face of the cylinder is fully closed and wherein a distal end face of the cylinder is arranged to seal the cylinder against the connecting rod, wherein at least one transfer port is provided through the piston in a manner to allow a fluid to flow between the distal side of the piston and the proximal side.

8. The auto-injector according to claim 7, characterized in that at least one gasket ring is arranged to seal the piston against the cylinder and/or the connecting rod against the distal end face of the cylinder.

9. The auto-injector according to claim 7, characterized in that the plunger spring is arranged in a longitudinal bore in the connecting rod and grounded at its distal end in the drive collar, wherein the proximal end of the plunger spring bears against the proximal face of the cylinder from inside.

10. The auto-injector according to claim 1, characterized in that the drive collar and the trigger button have respective snap arms arranged to snap into each other, wherein the snap arms are disengageable by pressing the trigger button.

11. The auto-injector according to claim 1, characterized in that a cap is arrangeable at the proximal end of the proximal portion, wherein barbs are provided in the cap for gripping a protective needle shield arranged to protect the needle in a manner to remove the protective needle shield when the cap is removed.

12. The auto-injector according to claim 11, characterized in that the barbs are arranged to be constrained by the detector sleeve from moving radially outward and disengaging the protective needle shield when the cap is arranged at the auto-injector.

* * * * *